United States Patent [19]
Latch et al.

[11] Patent Number: 6,072,107
[45] Date of Patent: Jun. 6, 2000

[54] RYEGRASS ENDOPHYTES

[75] Inventors: Garrick Cecil Morland Latch, Palmerston North; Michael John Christensen, Ashurst; Brian Anthony Tapper, Palmerston North; Herrick Sydney Easton, Palmerston North; David Edward Hume, Palmerston North; Lester Ronald Fletcher, Christchurch, all of New Zealand

[73] Assignee: New Zealand Pastoral Agriculture Research Institute Limited, Hamilton, New Zealand

[21] Appl. No.: 09/085,735

[22] Filed: May 27, 1998

[30] Foreign Application Priority Data

May 27, 1997 [NZ] New Zealand ............................ 314926

[51] Int. Cl.$^7$ ............................... A01H 5/00; A01H 5/10; A01H 15/00
[52] U.S. Cl. ...................... 800/320; 800/298; 435/254.1; 424/93.5
[58] Field of Search .................................... 800/298, 320, 800/265; 435/254.1; 424/93.5

[56] References Cited

U.S. PATENT DOCUMENTS 4,940,834   7/1990   Hurley ..................................... 800/200

FOREIGN PATENT DOCUMENTS

| 63905 | 10/1991 | Australia .......................... C12N 1/14 |
| 0 753 259 A2 | 1/1997 | European Pat. Off. ....... A01N 63/04 |
| 233083 | 2/1991 | New Zealand . |
| 96/39807 | 12/1996 | WIPO .............................. A01H 5/12 |

OTHER PUBLICATIONS

Fraser, M.L. et al. "The Role of Endophytes in Integrated Pest Management for Turf"; *Handbook of Integrated Pest Management for Turfgrass & Ornamentals*, (1994) CRC Press, Inc. pp. 521–528.

Funk, C.R. et al. "Role of Endophytes in Grasses Used for Turf and Soil Conservation"; *Biotechnology of Endophytic Fungi of Grasses*, Charles W. Bacon & James F. White, Jr. Eds. (1994) CRC Press, Inc. pp. 201–209.

Johnson, M.C. et al. "Infection of Tall Fescue with Acremonium coenophialum by Means of Callus Culture"; (1986) *Plant Disease* 70(5):380–382.

O'Sullivan, B.D. et al. "Infection of Plantlets, Derived from Ryegrass and Tall Fescue Meristems, with *Acremonium Endophytes*"; Proc. of the 2$^{nd}$ Symposium on Acremonium Grass Interactions, D.E. Hume, G.C.M. Latch & H.S. Easton, Eds., 1993, Palmerston North, New Zealand.

Barker, D.J. et al. "Effect of water deficit on alkaloid concentrations in perennial ryegrass endophyte associations" (1993) Hume D.E., Latch G.C.M. and Easton H.S. (Eds) Proc. of the Second International Symposium on Acremonium/Grass Interactions, pp. 67–71 AgResearch, Palmerston North, New Zealand.

Davies, E. et al. "Alkaloid concentrations in field–grown synthetic perennial ryegrass endophyte associations"(1993) Proceedings of the Second International Symposium on Acremonium/Grass Interactions, Hume, Latch & Easton (Eds) pp72–76.

Dymock, J.J. et al. "Effects of Endophyte produced Mycotoxins on Argentine Stem Weevil and the Cutwork *Graphania Mutans*" Proceedings of the 5$^{th}$ Australasian Conference on Grassland Invertebrate Ecology, (1989) Stahl, (Ed) DD Printing, Victoria, pp. 35–43.

Dymock, J.J. et al. "Novel combinations of endophytes in ryegrasses and fecues and their effects on Argentine Stem Weevil (*Listronootus bonariensis*) feeding" Proceedings of the 5$^{th}$ Australian Conference on Grassland Invertebrate Ecology, (1989) P.O. Stahle, (Ed). pp. 28–33.

Easton, H.S. "Ryegrasses" (1983) *Plant Breeding in New Zealand* Wratt G.S. and Smith H.C. (Eds) pp. 229–236.

Easton, H.S. "Will Endophyte Strain Affect Variety Performance?" (1993) Proceedings of the Second International Symposium on Acremonium/Grass Interactions. Hume, Latch & Easton (Eds). pp. 195–199.

Fletcher, L.R. et al. "Evaluation of several lolitrem–free endophyte/perennial ryegrass combinations" (1991) *New Zealand Grassland Assoc*. 53:215–219.

Gallagher, R.T. et al. "Tremorgenic Neurotoxins from Perennial Ryegrass Causing Ryegrass Staggers Disorder of Livestock: Structure Elucidation of Lolitrem B" (1984) *J. Chem. Soc. Chem. Commun*. 614–616.

Gaynor, D.L. et al. "Insect Resistance, Animal Toxicity and Endophyte–Infected Grass" (1986), Proceedings of the New Zealand Grassland Association., 47:115–120.

Latch, G.C.M. et al. "Endophytic Fungi Affect Growth of Perennial Rye Grass" (1985) *New Zealand Journal of Agricultural Research* 28:165–168.

Latch, G.C.M. et al. "Endophytes of Annual and Hybrid Ryegrasses" (1988) *New Zealand Journal of Agricultural Research* 31:57–63.

Latch, G.C.M. et al. "Lolium Endophytes—Problems and Progress" (1988) Proceedings of the Japanese Association of Mycotoxicology Supplement No. 1, Mycotoxins and Phycotoxins 220–223.

Latch, G.C.M. "Influence of Acremonium endophytes on perennial grass improvement" (1994) *New Zealand Journal of Agricultural Research* 37:311–318.

(List continued on next page.)

*Primary Examiner*—Lynette R. F. Smith
*Assistant Examiner*—Melissa L. Kimball
*Attorney, Agent, or Firm*—Greenlace Winner and Sullivan PC

[57] ABSTRACT

Selected endophytes of the genus Neotyphodium (formerly Acremonium) form stable synthetic combinations with ryegrass hosts (preferably *Lolium perenne*). The combinations have improved resistance to invertebrate pests and drought effects as compared to ryegrass cultivars not containing such endophytes. The particular combinations of the invention have reduced toxicity to livestock as compared to naturally occurring endophyte/ryegrass combinations. The six preferred endophytes are AR1, AR12, AR22, AR50, AR52 and AR56.

11 Claims, No Drawings

OTHER PUBLICATIONS

Latch, G.C.M. et al. "Artificial infection of grasses with endophytes" (1985) *Annals of Applied Biology* 107:17–24.

Latch, G.C.M. "Plant improvement using endophytic fungi" (1989) Proceedings of the XVI International Grassland Congress 345–346.

Latch, G.C.M. et al. "Ryegrass Endophyte, Incidence and Control" (1982) *New Zealand Journal of Agricultural Research* 25:443–448.

Latch, G.C.M. et al. "Five Endophytes of Lolium and Festuca in New Zealand" (1984) *Mycotaxon* vol. XX No. 2, 535–550.

Popay, A.J. et al. "Resistance to Argentine Stem Weevil in Perennial Ryegrass Infected with Endophytes Producing Different Alkaloids" (1995) Proc. $48^{th}$ NZ Plant Protection Conf. 229–236.

Rolston, M.P. et al. "Viability of Lolium Endophyte Fungus in Seed Stored at Different Moisture Contents and Temperatures" (1986) *New Zealand Journal of Experimental Agriculture* 14:297–300.

Rowan, D.D. et al. "Isolation of Feeding Deterrents against Argentine Stem Weevil from Ryegrass infected with the Endophyte *Acremonium loliae*" (1986) *Journal of Chemical Ecology* 12(3):647–658.

Rowan, D.D. et al. "An Efficient Method for the Isolation of Peramine, An Insect Feeding Deterrent Produced by the Fungus *Acremonium lolli*" (1989) *Journal of Natural Products* 52(1):193–195.

Rowan, D.D. et al. "Peramine, a Novel Insect Feeding Deterrent from Ryegrass Infected with the Endophyte *Acremonium loliae*" (1986) *J. Chem. Soc., Chem. Commun.* 935–936.

Siegel, M.R. et al. "Fungal Endophytes of Grasses" (1987) *Ann. Rev. Phytopathol.* 25:293–315.

Siegel, M.R. et al. "Acremonium Fungal Endophytes ofd Tall Fescue and Perennial Ryegrass: Significance and Control" (1985) *Plant Disease* 69:179–183.

Tapper, B.A. et al. "Detection and Measurement of the Alkaloid Peramine in Endophyte Infected Grass", (1989) *Journal of Chromatography* 463:133–138.

West, C.P. et al. "Role of Acremonium in drought, pest, and disease tolerances of grasses" (1993) Proceedings of the Second International Symposium on Acremonium/Grass Interactions, Plenary Papers. Hume, Latch & Easton (Eds). 131–140.

Williams, J.G.K. et al. "DNA polymorphism amplified by arbitrary primers are useful as genetic markers" (1990) *Nucleic Acids Research* 18(22):6531–6535.

Yoder, O.C. "*Cochliobolus Heterostrophus*, Cause of Southern Corn Leaf Blight" (1988) *Advances in Plant Pathology* 6:93–112.

Author unknown, "Unravelling the Ryegrass Endophyte Mystery" (1989) *AgriSearch*, Feb., p.16.

Barker et al. Proceedings of the Second International Symposium on Acremonium/Grass Interactions. pp. 59–61, 1993.

Christensen. Proceedings of the Second International Symposium on Acremonium/Grass Interactions. pp. 67–71, 1993.

De Battista et al. Agronomy Journal. 82:651–654, 1990.

RYEGRASS ENDOPHYTES

CROSS REFERENCE TO RELATED APPLICATIONS

This application claims priority from New Zealand Patent application No. 314926 filed May 27, 1997.

STATEMENT RE FEDERALLY SPONSORED RESEARCH AND DEVELOPMENT

Not applicable.

BACKGROUND TO THE INVENTION

It is known from New Zealand patent specification 233,083 that synthetic combinations of endophyte strain/herbage cultivar can be made which are resistant to pests and can be less toxic to grazing animals. The combinations were achieved by selecting combinations which produced relatively high levels of peramine and little or no lolitrem B.

It has been found that the ergopeptine alkaloid, ergovaline, was produced in a synthetic endophyte/perennial ryegrass combination which had little or no lolitrem B and that livestock grazing on the combination had an adverse physiological reaction to ergovaline under specific conditions.

It is an object of this invention to go some way towards avoiding the above mentioned disadvantages and achieving the aforementioned desiderata or at least to offer the public a useful choice.

SUMMARY OF THE INVENTION

This invention relates to selected endophytes in the genus Neotyphodium (formerly acremonium) which form stable synthetic combinations with ryegrass hosts, which combinations have improved resistance to invertebrate pests in comparison with the same grasses lacking endophyte and which have reduced toxicity to livestock as compared to naturally occurring endophyte/ryegrass combinations.

For the purposes of this specification the expression "synthetic endophyte/ryegrass combination" means the combination of an endophyte and a culturally improved ryegrass cultivar each of which has been isolated from nature, but the combination of which does not exist in nature.

Accordingly, in a first aspect, the invention may be said broadly to consist in an axenic culture of an endophyte which in synthetic combination with a ryegrass cultivar produces levels of peramine in excess of 5 ppm, levels of lolitrem B of less than 0.1 ppm and levels of ergovaline of less than 0.2 ppm.

In another embodiment the invention may be said broadly to consist in a synthetic combination of an endophyte as defined immediately above with a ryegrass cultivar.

In another embodiment, the invention may be said broadly to consist of an axenic culture of an endophyte selected from the group consisting of AR1, AR12, AR22, AR50, AR52 and AR56, AGAL deposit nos. NM98/04669, NM98/04670, NM98/0467 1, NM98/04672, NM98/04673 and NM98/04674, respectively on May 12, 1998.

In another embodiment the invention may be said broadly to consist in a synthetic combination of a ryegrass cultivar and an endophyte selected from AR1, AR12, AR22, AR50, AR52 and AR56.

In one alternative said ryegrass cultivar is a perennial ryegrass cultivar.

In another alternative said ryegrass cultivar is a hybrid ryegrass cultivar.

Preferably said ryegrass cultivar is a perennial ryegrass cultivar selected from the group consisting of Grasslands Nui, Grasslands Ruanui, Danny, Kosta, Grasslands Pacific, Borvi, Yatsunami, Grasslands Samson, Vedette, Bronsyn, Aries and Embassy.

Alternatively said ryegrass cultivar is a hybrid ryegrass cultivar selected from the group consisting of Grasslands Greenstone, Grasslands Impact, Grasslands Marsden, Maverick Gold, Te Puna, Coruna and Grasslands Supreme.

Preferably said synthetic combination is made by inoculating a said ryegrass cultivar with a said axenic culture of a said endophyte.

In another alternative said synthetic combination is made by crossing a said synthetic endophytic/ryegrass combination with an endophyte free ryegrass cultivar to form a new ryegrass cultivar infected with said endophyte.

The invention may also be said broadly to consist in seeds of said synthetic combination. Preferably said seeds are harvested from ryegrass plants inoculated with said endophyte. Alternatively, said seeds are harvested from plants of said synthetic endophytes/ryegrass combination grown from seeds harvested from ryegrass plants inoculated with said endophyte.

In another alternative the invention may be said broadly to consist in a synthetic endophyte/ryegrass plant combination substantially as herein described with reference to any example thereof.

DETAILED DESCRIPTION OF THE INVENTION

The invention consists in the foregoing and also envisages constructions of which the following gives examples.

EXAMPLE 1

Selected Endophytes

Endophytes AR1, AR12, AR22, AR50, AR52 and AR56

All endophytes other than AR22 are strains from collections of seed of perennial ryegrasses from Central Italy. AR22 is a strain from a seed collection from Spain. The endophytes are held in a culture collection at the Grasslands site in Palmerston North of the New Zealand Pastoral Agriculture Research Institute of New Zealand Limited (AgResearch). The cultures are also deposited at the Australian Government Analytical Laboratories in Sydney, Australia under numbers NM98/04669, NM98/04670, NM98/04671, NM98/04672, NM98/04673 and NM98/04674, respectively on May 12, 1998. AR1 is the subject of New Zealand Plant Varieties Right Grant No. 1079 of Apr. 23, 1996.

All six strains of endophytes can be accommodated within a single subgrouping of the taxon *Neotyphodium lolii*. These isolates when grown on potato dextrose agar at 22° C. are slow growing (radial growth rate less than 0.15 mm per day at 20° C.), with colonies typically raised, domed, white to tan, texture variable, ranging from cottony felted to waxy and with a pale brown underside. Instability in vitro can occur with resulting changes in the texture, shape and growth rate of colonies. Conidia have not been observed.

EXAMPLE 2

Identification of Endophytes by Polymorphic DNA Microsatellite Analysis

The endophytes AR1, AR12, AR22, AR50, AR52 and AR56 are distinguished from other groups of Neotyphodium endophytes occurring naturally in cultivars of *Lolium perenne* by the characterisation of alleles at one or more polymorphic genetic loci. The distinguishing characteristics are the number of distinct and the size of microsatellite sequences amplified by the polymerase chain reaction (PCR) technique using selected amplification primers.

Five sets of PCR primers pairs, one of each pair labelled with a fluorescent dye phosphoramidite at the 5'- end for detection purposes, have been selected to define the microsatellite loci for characterisations of endophyte in planta. The fluorescent dye labels are 6-carboxyfluorescein (6-FAM), 4,7,2', 7'-tetrachloro-6-carboxyfluorescein (TET) and 4,7,2',4',5',7'-hexachloro-6-carboxyfluorescein (HEX). The primer sequence pairs are as in Table 1.

The use of a fluorescent dye on just one primer of each primer pair gives the size measurement of only one of the strands of the amplified sequences of each allele, which simplifies the interpretation of results. The use of different dyes for loci where amplification products might occur in overlapping size ranges means that a single combination of PCR products can be analysed simultaneously for each endophyte.

The results for individual endophyte PCR microsatellite loci size analysis are considered in conjunction with information from other endophytes and interpreted bearing in mind that the PCR reaction using Taq polymerase tends to add a single additional adenine to amplification products. This gives a proportion of product one base higher in length than the actual sequence being amplified. The length of the

TABLE 1

Primer Sequence Pairs for Defining Microsatellite Loci of Endophyte in planta

| Locus | Primers | | Primer Sequences | 5'-Dye |
|---|---|---|---|---|
| B4 | B4.1 | (SEQ ID NO:1) | 5'-TGG ACT CGA CTT GCC CTC TCT CAG | FAM |
|    | B4.2 | (SEQ ID NO:2) | 5'-TGC GAG CAG CGT TTG CGT GTG CGT | |
| B6 | B6.1 | (SEQ ID NO:3) | 5'-GGC ATG GTA TGG GCA ATG AGT GT | FAM |
|    | B6.2 | (SEQ ID NO:4) | 5'-CTG CTG CGA TGT TTT GTA CTG TGG | |
| B9 | B9.1 | (SEQ ID NO:5) | 5'-AAT CGT TGT GCG AGC CAT TCT GT | TET |
|    | B9.4 | (SEQ ID NO:6) | 5'-GCC CCG TCA TGC ATT ATC TCC TTG | |
| B10 | B10.1 | (SEQ ID NO:7) | 5'-CGC TCA GGG CTA CAT ACA CCA TT | TET |
|     | B10.2 | (SEQ ID NO:8) | 5'-CTC ATC GAG TAA CGC AGG CGA CG | |
| B11 | B11.1 | (SEQ ID NO:9) | 5'-CAT GGA TGG ACA AGA GAT TGC AC | HEX |
|     | B11.4 | (SEQ ID NO:10) | 5'-TTC ACT GCT ACA ATT CTG TGG AGC | |

To characterise each endophyte a sample of genomic DNA is prepared from 100 mg to 200 mg fresh weight of pseudo-stems of endophyte-infected grass plants by the FastDNA Kit method for plant tissue (Bio 101, Inc., 1070 Joshua Way, Vista Calif., USA). The DNA is used for PCR amplification with the primer pairs either individually or combinations of primers pairs for loci B4 with B6, B9 with B10, and B11 alone.

The polymerase chain reactions are prepared in 12.5 μl volumes containing mM Tris-HCl, 1.5 mM MgCl$_2$, 50 mM KCl, pH 8.3 in the presence of 50 μM of each deoxynucleotide triphosphate, 200 nM of each primer, 0.08 U μl$^{-1}$ Taq DNA polymerase (Boehringer Mannheim GmbH) and approximately 400 pg μl$^{-1}$ total genomic DNA. The PCR is conducted for 30 cycles with temperature steps of 1 min at 94°, 2 min at 65°, and 1 min at 72° followed by a final extension of 10 min at 72° with a PC-960 or FTS-960 thermocycler (Corbett Research, Mortlake, Australia).

No PCR amplification product is observed when genomic DNA from plants lacking endophyte is used in PCR with the selected primer pairs.

Appropriate portions from the PCR amplifications for each endophyte sample, mixed together with GS-500 TAMRA as an internal size standard, are analysed by polyacrylamide gel electrophoresis (4.25%) on an ABI Prism 377 DNA Sequencer (Perkin-Elmer Corp., Foster City, Calif., USA). The size of the products is measured using GeneScan Analysis 2.1 software (Perkin-Elmer Corp.).

PCR product, considered for the purposes of comparing endophytes is the best estimate of the size actually amplified and may be one base less than the size reported by the GeneScan Analysis system. On occasions both the actual size and a size one unit greater may be resolved by the instrument and reported. For the purposes of comparing estimated sizes a tolerance of ±0.5 of a size unit may be accepted as being within a single size range after allowance has been made for the possibility of the PCR product being recorded as of one additional length unit in size.

The endophytes AR1, AR12, AR22, AR50, AR52 or AR56 can be distinguished by yielding a single B11 allele of 149.7 size units. The common *Neotyphodium lolii* endophytes of cultivars, which accumulate lolitrems, peramine, and ergovaline, yield a single B11 allele of either 176.9 units or 189.9 units. Otherwise the endophytes share single alleles of B4 at 100.2 units, B6 at 187.6 units, B9 at 247.4 units and B10 at 178.0 units.

The listed endophytes may also be distinguished from others of the type which may accumulate peramine and ergovaline but not lolitrems as described in New Zealand patent specification 233083 (NZP 233083). Those endophytes yield an additional B4 allele at 120.3, B6 allele at 187.6 and B10 allele at 169.2 units. Results are summarised in Table 2.

TABLE 2

Summary of Microsatellite Data for Distinguishing the Endophytes

| Locus | Allele size(s) AR1, AR12, AR22 AR50, AR52 & AR56 | Allele size(s) Common N. lolii | Allele size(s) NZP 233083 type |
|---|---|---|---|
| B4 | 100.2 | 100.2 | 100.2 & 120.3 |
| B6 | 187.6 | 187.6 | 171.1 & 187.6 |
| B9 | 247.4 | 247.4 | 247.4 |
| B10 | 178.0 | 178.0 | 169.3 & 178.0 |
| B11 | 149.7 | 176.9, 180.9 or 188.9 | 119.7 |

The endophytes AR1, AR12, AR22, AR50, AR52 or AR56 thus form a distinct group by polymorphic DNA microsatellite analysis, different from any other described grouping or classification of *Neotyphodium lolii* endophytes.

EXAMPLE 3

Isolation of Endophytes from their Natural Host (a) From plants

Leaf sheath tissue of ryegrass plants containing natural endophytes was removed from the plant and surface sterilized by dipping it into 70% ethanol for 5 seconds before placing it in a 10% solution of sodium hypochlorite (0.5% available chlorine) and shaking for 5 minutes. The tissue was then rinsed in sterile water and cut into 2–3 mm pieces.

(b) From seed

Ryegrass seeds containing endophyte were surface sterilized by soaking for 20 minutes in 50% sulphuric acid followed by rinsing several times in sterile water, soaking in 10% sodium hypochlorite solution for 20 minutes and rinsing again in sterile water. All surface sterilized tissues were placed on potato dextrose agar containing antibiotics (100 μ/ml streptomycin+100 μg/ml penicillin) in Petri dishes and incubated at 20° C. for 4–5 weeks. By this time colonies of endophytes had sufficient growth to enable them to be used for inoculating grass seedlings.

EXAMPLE 4

Inoculation of Seedlings (a) Growing of Seedlings for Inoculation

Inoculation of seedlings is done in a sterile environment so it is necessary to surface sterilize the seeds before they are germinated. The seeds are soaked for 20 minutes in a 50% solution of sulphuric acid in water, washed in sterile water, soaked for 20 minutes in a 20% solution of a chlorine based bleach sold under the trade mark "Janola" and then washed in sterile water. The seeds are then dried on sterile filter paper in a laminar flow cabinet. These dried seeds are placed 10/plate on the surface of 4% water agar in Petri plates and incubated in the dark at 20° C. for 5–7 days. The plates are examined daily for contaminant fungi not killed by surface sterilization and contaminated seedlings are removed with a scalpel.

(b) Inoculation of Seedlings

Colonies of endophyte are grown on Potato Dextrose Agar in Petri plates at 20° C. Ryegrass seedlings which are 5–7 days old are inoculated with endophyte mycelium by making a longitudinal slit with a scalpel in the meristematic region of the seedling stem. Mycelium is introduced into the slit with a needle or scalpel. The Petri plates are sealed with tape and incubated in the dark at 20° C. for 2–4 days. The plates are then removed and placed on a bench in the light or in an illuminated incubator for 3–4 days prior to planting the seedlings in compost-filled root-trainers.

EXAMPLE 5

Growing of Seedling and Harvesting of Seeds

Infected ryegrass seedlings, after testing for verification of infection with the candidate endophyte, were naturally vernalised through the winter and placed in isolation with other ryegrass plants of the same cultivar (so that pollen from ryegrass not of the same cultivar was excluded). When seed was set, the originally infected isolated plants were harvested individually. A sample of seed from each infected isolated plant was tested to verify the presence and identity of endophyte within the seed. A sample of seed from each infected isolated plant was sown to verify that progeny plants conformed to the description of the original inoculated cultivar. Plants originally infected with the same endophyte strain, and for which seed passed the above two tests, were defined as the "infected parent plants" for that strain. The seed from the different infected parent plants was bulked (the same weight from each infected parent plant) to form a seed lot which was subsequently multiplied under normal seed certification procedures, with the frequency of endophyte infection of each harvest verified by seed squash.

EXAMPLE 6

Measurement of Alkaloids

Seeds and herbage from ryegrass plants separately infected with each of AR1, AR12, AR22, AR50, AR52 and AR56 were grown in a glasshouse at 18–22° C., and freeze dried, ground and analysed by high pressure liquid chromatography (HPLC) for the alkaloids peramine, lolitrem B and ergovaline by the method of Barker et al. (1993).

The ranges of levels detected in herbage are set out below in Table 3.

TABLE 3

Concentrations of Alkaloids - measured in parts per million

| Peramine | Lolitrem β | Ergovaline |
|---|---|---|
| >5 | <0.1 | <0.2 |

EXAMPLE 7

Agronomic Trials

Four replicated field trials in the Manawatu district, New Zealand comparing the growth of Grasslands Nui plants infected with the 6 listed endophytes or with wild-type endophytes and with endophyte-free Grasslands Nui have been conducted over a period of up to 2 years. All endophyte-infected plants showed significantly more herbage growth then endophyte-free Grasslands Nui and in some trials the plants infected with the endophytes listed in this patent produced more herbage than Nui plants infected with wild-type endophytes. Table 4 summarises the cumulative ryegrass herbage yield from one of the trials at Palmerston North, New Zealand over the 1997/98 season.

TABLE 4

Herbage Yield from Grasslands Nui Perennial Ryegrass Infected with Different Endophyte Strains Compared with Endophyte-Free Nui

| Endophyte strain | AR1 | AR12 | AR22 | Wild-type | Endo-free |
|---|---|---|---|---|---|
| Cumulative herbage dry weight (gm) | 18,515 | 19,483 | 18,837 | 18,758 | 16,763 |

All endophyte-infected plots produced significantly more herbage than the endophyte-free plots.

Trials with AR50, AR52 and AR56 have only recently been conducted and preliminary results indicate that there are no significant differences in herbage yield between Nui perennial ryegrass infected with those strains and that of Nui infected with wild-type endophytes.

Replicated trials at 6 sites throughout New Zealand compared dry matter yield and Argentine stem weevil damage of Grasslands Nui perennial ryegrass infected with wild-type and with AR1, AR12 and AR22 strains. As a control, endophyte-free Nui was included. The trials have been conducted for 2 years and results have shown no significant difference in herbage production between wild-type and any of the synthetic combinations of Nui and AR1, AR12 and AR22 in dry matter yield or Argentine stem weevil damage. All endophyte-infected plots yielded more dry matter than endophyte-free plots and suffered less Argentine stem weevil damage.

EXAMPLE 8

Animal Feeding Trials

Separate, replicated pastures were sown in 1996 at Lincoln, New Zealand with Grasslands Nui perennial ryegrass free of endophyte, infected with wild-type endophytes or with AR1 endophyte. These pastures were grazed with 6 month-old Coopworth ewe lambs. The various lamb responses after the first year of the trial are set out in Table 5 and show no difference between endophyte-free and AR1 but a significant difference between wild-type and these two treatments.

TABLE 5

Lamb Response to Grazing Nui Ryegrass with AR1 Endophyte - 1996/97

| | Live Wt. Gain gm/head/day | Body Temp. ° C. | Respiration rate/30 sec. | Prolactin ng/ml | Ryegrass staggers 1–5 score |
|---|---|---|---|---|---|
| Wild-type | 50 | 40.6 | 101 | 124 | 3.8 |
| Endo.-free | 105 | 40.3 | 78 | 184 | 0 |
| AR1 | 140 | 40.3 | 84 | 207 | 0 |

This trial was continued for a further year and the results from the second year are presented in Table 6. They show that there was a significant difference in live weight gain, temperature and respiration in both spring and summer between the lambs on the wild-type endophyte pastures and those on the AR1 pastures. Ryegrass staggers only developed in summer and there was significantly more staggers in lambs on the wild-type pastures than with those on AR 1.

TABLE 6

Lamb Response to Grazing Nui Ryegrass with AR1 Endophyte - 1997/98

| | Live Wt. Gain gm/head/day | Body Temp. ° C. | Respiration rate/30 sec. | Ryegrass staggers 1–5 score |
|---|---|---|---|---|
| SPRING | | | | |
| Wild-type | 55 | 40.3 | 93 | 0 |
| Endo-free | 75 | 40.0 | 83 | 0 |
| AR1 | 124 | 40.2 | 88 | 0 |
| SUMMER | | | | |
| Wild-type | −39 | 40.0 | 82 | 3.5 |
| Endo-free | 72 | 39.5 | 54 | 0.1 |
| AR1 | 98 | 39.6 | 63 | 0.1 |

A similar trial was sown in 1997 and the effects of the different treatments on the lambs grazing this trial in the summer of 1997/98 are given in Table 7. As with the previous trial, the lambs grazing AR1 had significantly greater live weight gain, lower temperature and respiration and less ryegrass staggers than did the lambs grazing wild-type endophyte-infected Nui pastures. There was evidence of mild ryegrass staggers in some the lambs grazing AR1 but this must be considered in the context of the extreme levels of staggers in wild-type control treatments and that ryegrass staggers in surrounding commercial flocks was the most serious it had been in 20 years.

TABLE 7

A Second Trial to Show Lamb Response to Grazing Nui Ryegrass with AR1 in Summer 1997/98

| | Live Wt. Gain gm/head/day | Body Temp. ° C. | Respiration rate/30 sec. | Ryegrass staggers 1–5 score |
|---|---|---|---|---|
| Wild-type | 16 | 40.6 | 97 | 4.5 |
| Endo-free | 125 | 40.2 | 73 | 0 |
| AR1 | 102 | 40.3 | 76 | 1.0 |

EXAMPLE 9

Insect Trials

Controlled greenhouse feeding trials compared the damage caused by Argentine stem weevil larvae on endophyte-free Grasslands Nui ryegrass plants with that on plants infected with the endophytes listed in the patent or with wild-type endophytes. Tiller damage in all the endophyte-infected plants was significantly less than in the endophyte-free plants. Detailed results are given in Tables 8, 9 and 10.

TABLE 8

Evaluation of AR1 for Resistance to Argentine Stem Weevil

| | Adult feeding/tiller | | No. Eggs/Tiller | | % tillers with larval damage | |
|---|---|---|---|---|---|---|
| Endophyte | Spring | Summer | Spring | Summer | Spring | Summer |
| AR1 | 0.73 | 1.05 | 0.09 | 0.02 | 0.9 | 2.5 |
| Wild-type | 0.60 | 0.95 | 0.06 | 0.03 | 5.8 | 2.5 |
| Endo-free | 2.16 | 2.16 | 0.38 | 0.27 | 30.8 | 15.0 |

TABLE 9

Evaluation of AR12 and AR22 for Resistance to Argentine Stem Weevil

| Endophyte | Adult feeding/tiller | No. Eggs/tiller | % tillers with larval damage |
|---|---|---|---|
| AR12 | 2.28 | 8.15 | 25.90 |
| AR22 | 2.22 | 11.65 | 22.30 |
| Wild-type | 2.09 | 7.60 | 23.50 |
| Endo-free | 2.89 | 17.13 | 48.70 |

In the above table adult feeding was not significantly reduced by any endophyte but there were significantly fewer eggs on plants infected with AR12 and wild-type endophytes. All endophytes significantly reduced larval damage.

TABLE 10

Greenhouse Screening Trial to Evaluate Argentine Stem Weevil Behaviour on Nui Ryegrass Plants Infected with AR50, AR52, AR56, Wild-Type Endophytes and with Endophyte-Free Plants

| Endophyte | Adult feeding/tiller | No. Eggs/plant | % tillers with larval damage |
|---|---|---|---|
| AR50 | 1.20 | 4.8 | 14 |
| AR52 | 1.62 | 2.9 | 10 |
| AR56 | 2.22 | 3.9 | 8 |
| Wild-type | 0.88 | 4.7 | 0 |
| Endo-free | 1.50 | 4.6 | 27 |

AR52 and AR56 had significantly less weevil damage than the endophyte-free ryegrass.

Data on weevil occurrence and damage was recorded from October to March in the endophyte evaluation trials at 6 sites throughout New Zealand. Table 11 gives the results at the 6 sites for the month of February.

TABLE 11

Occurrence and Damage from Argentine Stem Weevil on the Endophyte Evaluation Trials at Six Sites in New Zealand

| Endophyte | Adult feeding/tiller | No. Eggs/plant | % tillers with larval damage |
|---|---|---|---|
| AR1 | 0.97 | 0.10 | 7.5 |
| AR12 | 0.97 | 0.07 | 3.0 |

TABLE 11-continued

Occurrence and Damage from Argentine Stem Weevil on the Endophyte Evaluation Trials at Six Sites in New Zealand

| Endophyte | Adult feeding/tiller | No. Eggs/plant | % tillers with larval damage |
|---|---|---|---|
| Wild-type | 0.91 | 0.04 | 4.3 |
| Endo-free | 1.46 | 0.14 | 23.1 |

When compared with the endophyte-free plots the endophyte-infected treatments had significantly fewer weevils and eggs and less larval damage.

Mean numbers of adult Argentine stem weevils were also counted on the grazing trials conducted with Nui perennial ryegrass with AR1 or wild-type endophytes and endophyte-free ryegrass. The results are given in Table 12.

TABLE 12

Effect of Endophyte Infection on Argentine Stem Weevil Numbers in Nui Ryegrass Grazing Trials

| | Numbers of adult Argentine Stem Weevil/Square m | |
|---|---|---|
| Endophyte | 1997 | 1998 |
| AR1 | 6 | 17 |
| Wild-type | 10 | 22 |
| Endo-free | 37 | 96 |

There were significantly more weevils on the endophyte-free ryegrass than on the endophyte-infected pastures.

REFERENCE

Barker, D. J., Davies, E., Lane, G. A., Latch, G. C. M., Nott, H. M. and Tapper, B. A 1993. Effect of water deficit on alkaloid concentrations in perennial ryegrass endophyte associations. Hume, D. E., Latch, G. C. M. and Easton, H. S (eds.) Proc. Second International Symposium on Acremonium Grass Interactions, pp.67–71. AgResearch, Palmerston North, New Zealand.

---

What is claimed is:

1. An axenic culture of an endophyte selected from the group consisting of AR1, AR12, AR22, AR50, AR52 and AR56, AGAL deposit nos. NM98/04669, NM98/04670, NM98/04671, NM98/04672, NM98/04673 and NM98/04674, respectively.

2. A synthetic combination of an endophyte as claimed in claim 1 with a ryegrass cultivar selected from *Lolium perenne* and hybrid cultivars thereof.

3. A combination as claimed in claim 2 wherein said ryegrass cultivar is a *Lolium perenne* cultivar.

4. A combination as claimed in claim 2 wherein said ryegrass cultivar is a hybrid ryegrass cultivar.

5. A combination as claimed in claim 2 wherein said ryegrass cultivar is selected from the group consisting of Grasslands Pacific, Grasslands Samson, Vedette, Bronsyn, and Embassy.

6. A combination as claimed in claim 2 wherein said ryegrass cultivar is selected from the group consisting of Grasslands Greenstone, Grasslands Impact and Maverick Gold.

7. A combination as claimed in claim 2 which has been made by inoculating a said ryegrass cultivar with a said axenic culture of a said endophyte.

8. A combination as claimed in claim 2 which has been made by crossing a said synthetic endophyte/ryegrass combination with an endophyte free ryegrass cultivar selected from *Lolium perenne* and hybrid cultivars thereof to form a ryegrass cultivar cross infected with said endophyte.

9. Seeds as a combination as claimed in claim 2.

10. Seeds as claimed in claim 9 which have been harvested from said ryegrass cultivar plants inoculated with said endophyte.

11. Seeds as claimed in claim 9 which have been harvested from plants of said synthetic endophytes/ryegrass combination grown from seeds harvested from said ryegrass cultivar plants infected with said endophyte or from seeds of subsequent generations of said ryegrass cultivar plants so infected.

* * * * *

UNITED STATES PATENT AND TRADEMARK OFFICE
CERTIFICATE OF CORRECTION

PATENT NO. : 6,072,107
DATED : June 6, 2000
INVENTOR(S) : Latch et al.

Page 1 of 1

It is certified that error appears in the above-identified patent and that said Letters Patent is hereby corrected as shown below:

Title page,
After "Attorney, Agent, or Firm" delete "Greenlace" and replace with -- Greenlee --.

Column 3,
Table 1, delete the entire Table 1 and replace with the following:

--TABLE 1.

**Primer Sequence Pairs for Defining Microsatellite Loci of Endophyte *in planta***

| Locus | Primers | Seq Id No. | Primer Sequences | 5'- Dye |
|---|---|---|---|---|
| B4 | B4.1 | (SEQ ID NO: 1) | 5'-TGG ACT CGA CTT GCC CTC TCT CAG | 6-FAM |
|  | B4.2 | (SEQ ID NO: 2) | 5'-TGC GAG CAG CGT TTG CGT GTG CGT |  |
| B6 | B6.1 | (SEQ ID NO: 3) | 5'-GGC ATG GTA TGG GCA ATG AGT GTC | 6-FAM |
|  | B6.2 | (SEQ ID NO: 4) | 5'-CTG CTG CGA TGT TTT GTA CTG TGG |  |
| B9 | B9.1 | (SEQ ID NO: 5) | 5'-AAT CGT TGT GCG AGC CAT TCT GGC | TET |
|  | B9.4 | (SEQ ID NO: 6) | 5'-GCC CCG TCA TGC ATT ATC TCC TTG |  |
| B10 | B10.1 | (SEQ ID NO: 7) | 5'-CGC TCA GGG CTA CAT ACA CCA TGG | TET |
|  | B10.2 | (SEQ ID NO: 8) | 5'-CTC ATC GAG TAA CGC AGG CGA CG |  |
| B11 | B11.1 | (SEQ ID NO: 9) | 5'-CAT GGA TGG ACA AGA GAT TGC ACG | HEX |
|  | B11.4 | (SEQ ID NO: 10) | 5'-TTC ACT GCT ACA ATT CTG TGG AGC-- |  |

Claim 9,
Delete "Seeds as" and replace with -- Seeds of --.

Signed and Sealed this

Eleventh Day of September, 2001

Attest:

NICHOLAS P. GODICI
Attesting Officer
*Acting Director of the United States Patent and Trademark Office*

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(iii) HYPOTHETICAL: NO (xi) SEQUENCE DESCRIPTION: SEQ ID NO:1:

TGGACTCGAC TTGCCCTCTC TCAG                                              24

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:2:

TGCGAGCAGC GTTTGCGTGT GCGT                                              24

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:3:

GGCATGGTAT GGGCAATGAG TGTC                                              24

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:4:

CTGCTGCGAT GTTTTGTACT GTGG                                              24

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:5:

AATCGTTGTG CGAGCCATTC TGGC                                              24

(2) INFORMATION FOR SEQ ID NO:6:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "oligonucleotide"

(iii) HYPOTHETICAL: NO (xi) SEQUENCE DESCRIPTION: SEQ ID NO:6:

GCCCCGTCAT GCATTATCTC CTTG                                              24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:7:

CGCTCAGGGC TACATACACC ATGG                                              24

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:8:

CTCATCGAGT AACGCAGGCG ACG                                               23

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:9:

CATGGATGGA CAAGAGATTG CACG                                              24

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear -continued

```
    (ii) MOLECULE TYPE: other nucleic acid
         (A) DESCRIPTION: /desc = "oligonucleotide"

(iii) HYPOTHETICAL: NO (xi) SEQUENCE DESCRIPTION: SEQ ID NO:10:

TTCACTGCTA CAATTCTGTG GAGC                                            24
```